United States Patent [19]

Kaukler

[11] Patent Number: 4,711,697
[45] Date of Patent: Dec. 8, 1987

[54] METHOD FOR INVESTIGATING THE FORMATION OF CRYSTALS IN A TRANSPARENT MATERIAL

[75] Inventor: William F. Kaukler, Huntsville, Ala.

[73] Assignee: The United States of America as represented by the Administrator of the National Aeronautics and Space Administration, Washington, D.C.

[21] Appl. No.: 800,194

[22] Filed: Nov. 21, 1985

[51] Int. Cl.[4] .......................... B01J 17/08; B01D 9/00
[52] U.S. Cl. .................................... 156/621; 156/622; 156/624; 422/251; 422/260
[58] Field of Search ........................ 374/17, 18, 16, 20, 374/160; 356/30, 31; 156/601, 621; 422/260, 251

[56] References Cited

U.S. PATENT DOCUMENTS

| | | | |
|---|---|---|---|
| 2,571,651 | 10/1951 | Balduzzi | 156/601 |
| 2,721,495 | 10/1955 | Schaefer | 374/16 X |
| 2,750,433 | 6/1956 | LeTourneau et al. | 374/16 X |
| 3,243,320 | 3/1966 | Namazu et al. | 156/601 X |
| 4,028,941 | 6/1977 | Henderson et al. | 374/159 |
| 4,096,024 | 6/1978 | Dusserve et al. | 156/601 |

OTHER PUBLICATIONS

"The Review of Scientific Instruments", Dr. William Kaulker, Hot Stage and Sample Cell Design, etc., vol. 55, No. 10, pp. 1643-1647.

Primary Examiner—Daniel M. Yasich
Attorney, Agent, or Firm—Joseph H. Beumer; John R. Manning; Leon D. Wofford, Jr.

[57] ABSTRACT

A method of observing crystal formation in a transparent specimen (58 of FIG. 5) comprising the steps of melting a portion of the specimen in a heating zone (22 of FIG. 2) freezing the melted portion of the specimen 58 by a cooling zone (20 of FIG. 2) spaced from the heating zone by a gap (42) which is observable by a suitable observing means (30), controlling the temperatures of the heating and cooling zones (22 and 20) to various temperatures to create a variable temperature gradient across the gap (42) so that the freezing isotherm of the specimen (58) always remains in a substantially constant position within the gap (42) where it is observable by the observing means (30), and moving the specimen (58) longitudinally while the temperature gradient is varying.

20 Claims, 7 Drawing Figures

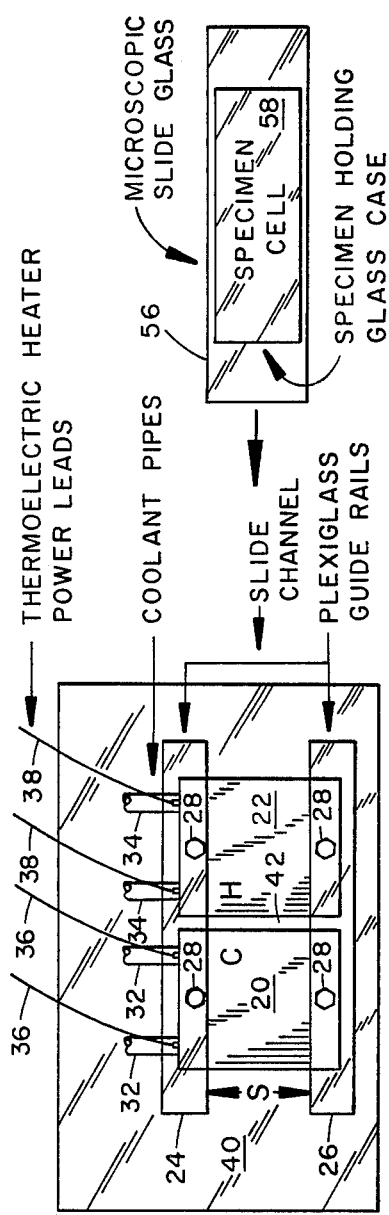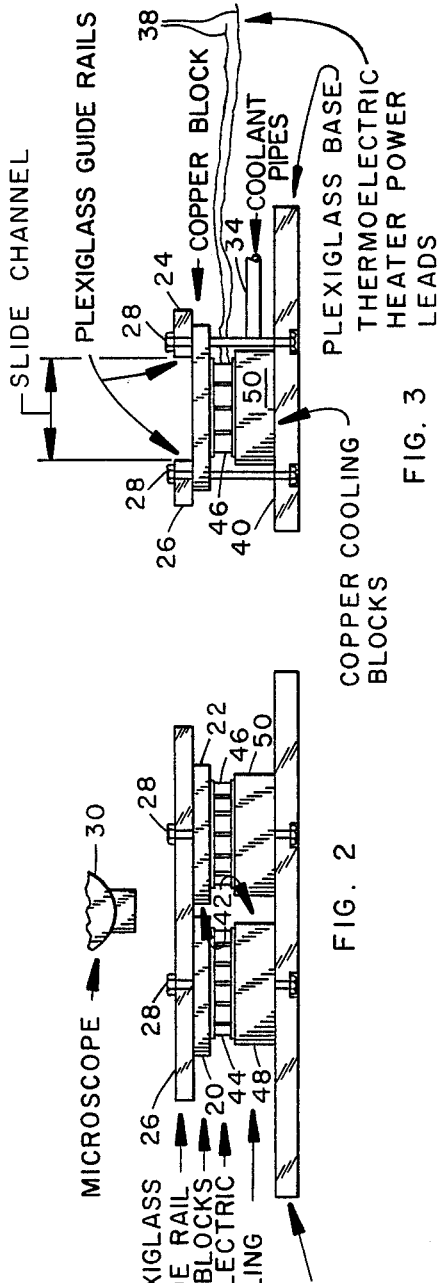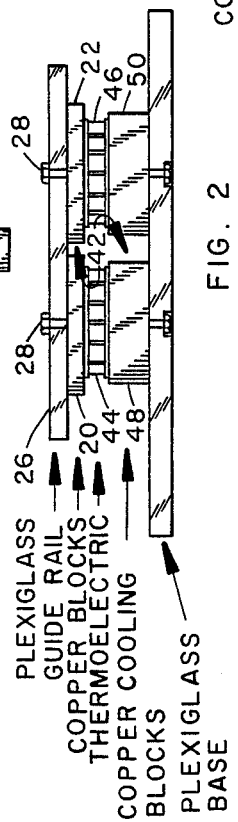

4,711,697

METHOD FOR INVESTIGATING THE FORMATION OF CRYSTALS IN A TRANSPARENT MATERIAL

ORIGIN OF THE INVENTION

The invention described herein was made in the performance of work under a NASA contract and is subject to the provisions of Public Law 96-517 (94 Stat 3019; 35 USC 200-211).

TECHNICAL FIELD

This invention relates generally to the formation of crystals and more particularly to a method and apparatus, for visually investigating and observing the characteristics of crystal growth while it is in progress.

BACKGROUND OF THE INVENTION

There are in the prior art many reports and results of studies of the nature of crystal growth by varying the rate of the crystal formation over time. Many of these prior art studies have been made with transparent specimen materials to enable an observer, with the aid of a microscope and various electronic and photographic or other display means, to study in some details the formation of crystals as the crystal forming material is passed through a constant temperature gradient G zone at a variable rate of velocity R from a heated area of constant temperature to a cooling area of constant temperature with the freezing zone lying directly under a microscope. The crystal growing material is in a molten state as it leaves the heated area and freezes as it enters the cooling area.

Such studies have particular importance in the field of metallurgy and specifically in metal and metal alloy casting processes.

For more detailed descriptions of these prior art studies reference is made to a publication entitled "Solidification", which is a collection of papers presented at a seminar of the American Society for Metals on Oct. 11-12, 1969 and published by the American Society for Metals in Metals Park, Ohio, and copyrighted in 1971, and another publication entitled "A Quantitative Study of Factors Influencing Lamellar Eutectic Morphology During Solidification" by WFS Kaukler of the Space Sciences Laboratory, NASA, at the George C. Marshall Space Flight Center, in Huntsville, Al., in November, 1981, and further identified as NASA TM-82451, both of which are incorporated herein by reference.

While these prior art studies have revealed much valuable information about the growth of crystals, many questions relating thereto remain unanswered.

It is a primary object of this invention to provide a new and novel process for visually observing and studying the growth of crystals under controllable variable conditions never done heretofor.

It is another object of the invention to provide a method of investigating crystal growth with a variable temperature gradient G which is controllable to maintain the freezing isotherm of the specimen material at a substantially constant, unmoving position which always lies under the objective lens of the fixed position microscope.

Another object of the invention is to provide a method and apparatus for investigating crystal growth in a transparent material with controllable variable temperature gradient G which is positionable to maintain the melting point isotherm of the transparent material at a substantially constant, unmoving position under a fixed position microscope while said transparent material is moving at a rate R in a transverse direction under the microscope at a controllable rate of speed.

Yet another object of the invention is to investigate crystal growth in a transparent material which is movable at a controllable, variable rate from a heated or melting zone to a cooling or freezing zone with the temperatures of the heating and cooling zones being variable in a controlled manner to create a variable temperature gradient at the freezing isotherm and to maintain the freezing or solidifying isotherm of the transparent material in a fixed position under the objective lens of a microscope.

Still another object of the invention is an improved and novel method and apparatus for studying crystal growth in a moving transparent material by varying the temperature gradient across the freezing point of the transparent material with said freezing point remaining in a fixed position relative to a fixed position observing means.

BRIEF SUMMARY OF THE INVENTION

In accordance with one preferred form of the invention there is provided a method of observing crystal formation in a transparent specimen comprising the steps of melting a portion of the specimen in a heaing zone, freezing the melted portion of the specimen in a cooling zone spaced from the heating zone by a gap in which the freezing isotherm of the specimen is observable by a suitable observing means, controlling the temperature of the heating and cooling zones to various temperatures to create a variable temperature gradient across the gap so that the freezing isotherm of the specimen always remains in a substantially constant position within the gap where it is observable by the stationary observing means, and moving the specimen longitudinally in order to cause unidirectional freezing of the molten material while the temperature gradient is varying in order to cause unidirectional freezing of the molten material.

BRIEF DESCRIPTION OF THE DRAWINGS

FIGS. 1, 2, and 3 respectively show a top view, a side view, and an end view of the invention;

FIG. 4 shows a generalized top view of the specimen on a microscope slide;

DETAILED DESCRIPTION OF THE INVENTION

Figure 5:
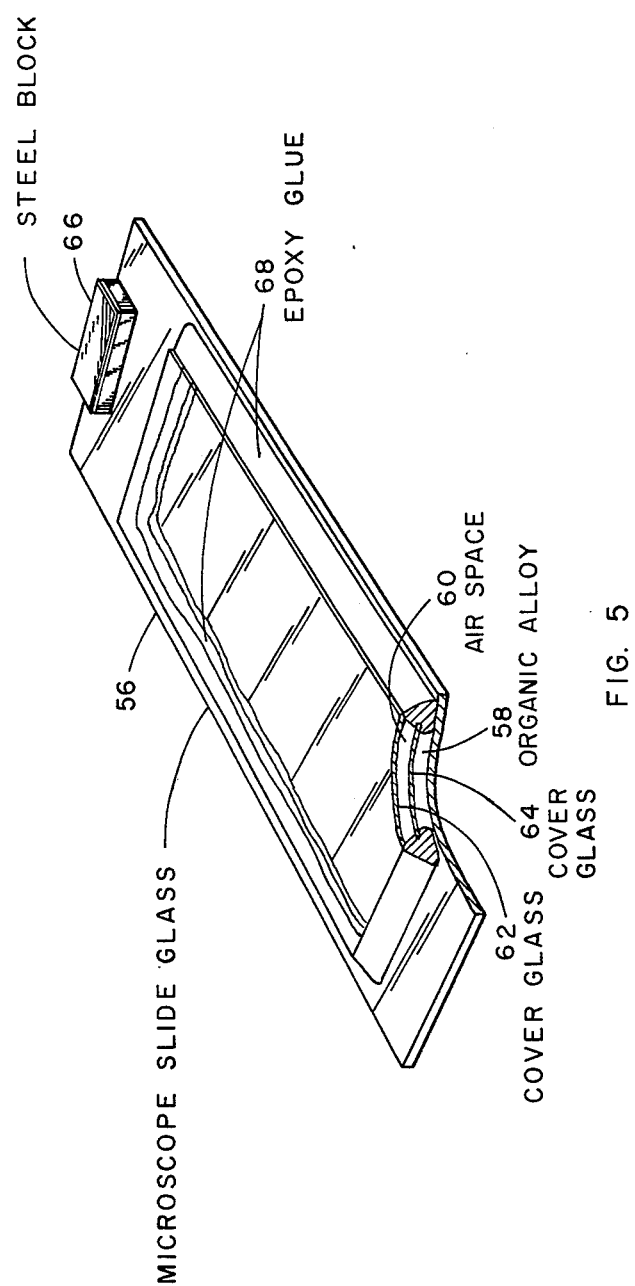
FIG. 5 is an isometric, detailed broken away view of the microscope glass slide and the structure holding the specimen thereon.

Referring now to FIGS. 1 and 2 there are shown a top view and a side view, respectively, of the invention. As can be seen from FIG. 2 there is mounted on a plexiglass base 40 a pair of copper cooling blocks 48 and 50, a pair of thermoelectric heaters 44 and 46, a copper heating source 22 and a copper cooling sink 20, and finally, as shown in FIG. 1, a pair of plexiglass guide rails 24 and 26, all held together in a stacked manner in the order recited by the four bolts 28. The specimen cell 58, mounted on microscope slide 56, as shown in FIG.

4, slides within the spacing S of FIG. 1 formed by the parallel inner edges of plexiglass guide rails 24 and 26 and upon the copper heating source 22 and cooling sink 20.

Figure 6:
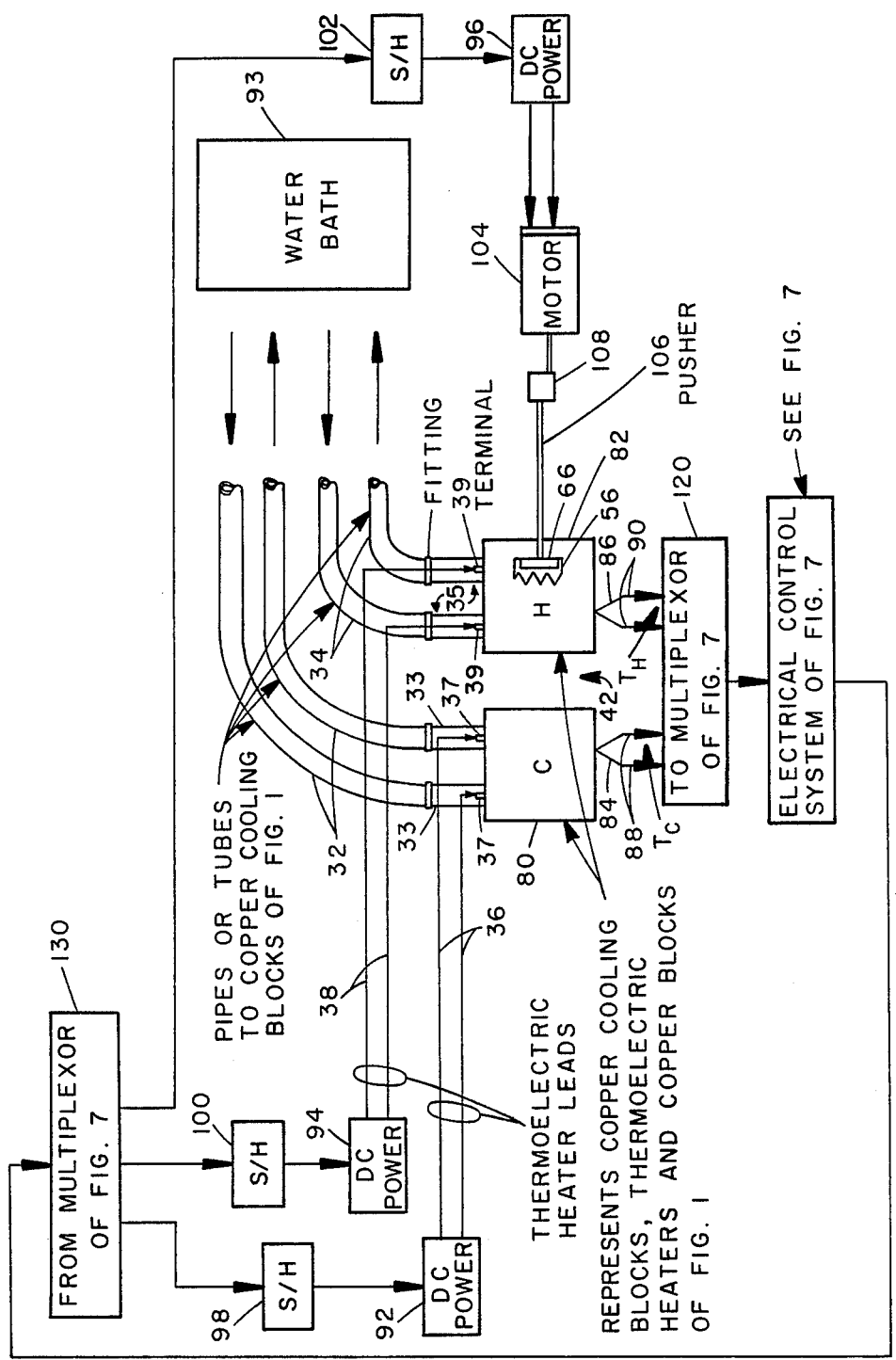
FIG. 6 is a broad block diagram of the overall system.

Two pairs of pipes 32 and 34 supply a suitable liquid coolant from a common source 93, shown in FIG. 6, to the two copper cooling blocks 48 and 50. One of each of the two pairs of pipes 32 and 34 is a coolant liquid inlet and the other is a coolant liquid outlet. Two pairs of leads 36 and 38 each connect d.c. current from two separate power sources 92 and 94 of FIG. 6. As can be clearly seen in FIG. 2 the aligned gaps 42 between the pair of copper blocks 20 and 22 and the pair of copper cooling blocks 48 and 50 allow an observer to view the slide 56 of FIG. 4 as it passes under the microscope 30 which is positioned to view directly into the gaps 42.

The end view of FIG. 2, shown in FIG. 3, more clearly shows the relationship between the coolant carrying pipes 34 and the copper cooling block 50, the leads 38 which carry d.c. power to the thermoelectric piles (heating devices) 46, and the depth of the microscope slide channel S.

In FIG. 5 the details of the specimen carrying slide 56 can be seen. A pair of cover glass plates 62 and 64, spaced apart by a small gap 60 of predetermined size from 25 to 250 micrometers, are mounted securely in that position on top of the microscope slide glass 56 by a suitable binder 68 such as an epoxy glue which extends entirely around the edges of the two cover glasses 62 and 64 to seal the gap inbetween airtight.

However, before the two cover glasses are securely sealed together the organic alloy specimen 58 to be melted and then frozen is inserted between the two cover glasses 62 and 64.

A steel block 66 is secured at one end of the microscope slide glass 56 to provide a means for a water-powered push rod 106 (see FIG. 6) to push the microscope slide glass along its guide path S, as shown in FIGS. 1 and 3.

Referring now to FIG. 6 the blocks 80 and 82, the coolant carrying pipes 32 and 34, and the thermoelectric heater leads 36 and 38, represent generally the entire structure of FIGS. 1, 2, 3, and 4. Added to FIG. 6 are terminals 37 and 39 to which heater leads 36 and 38 are connected, and fittings 35 to which coolant carrying pipes 32 and 34 are connected.

Figure 7:
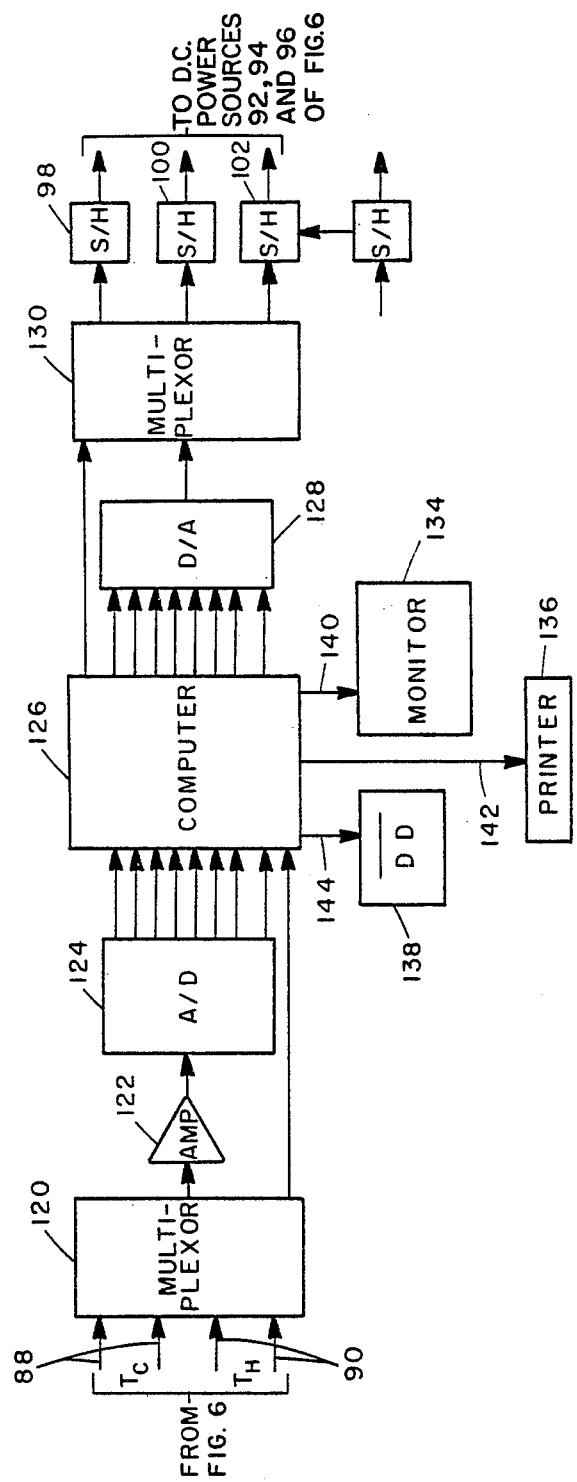
FIG. 7 is a block diagram of the electronics of the system.

Also added to FIG. 6 are the thermocouples 84 and 86 which detect the temperature of copper heating source 22 of FIG. 1 and cooling sink 20 of FIG. 1, and convert the detected temperatures to electrical signals which are supplied via leads 88 and 90 to multiplexor 120 of FIG. 7.

It should be noted that the liquid coolant to both copper heating blocks 48 and 50 (FIG. 2) comes from and returns to the same coolant source 93 of FIG. 6 so that the liquid coolant to both copper heating blocks 48 and 50 leaves the common coolant source 93 at the same temperature.

As will be discussed later in connection with FIG. 7 the power generated by d.c. power sources 92, 94, and 96 is controlled by the outputs of sample and hold (S/H) circuits 98, 100, and 102, respectively, and is supplied, respectively, to copper cooling sink 20 (of FIG. 2) and included within block 80 of FIG. 6, copper heating sink 22 (of FIG. 2) and included within block 82 of FIG. 6, and to motor 104. The motor 104 drives pusher rod 106 in a linear direction from right to left in FIG. 6 through adjustable speed reducing and worm gear arrangement 108 to in turn push microscope slide glass 56 by means of steel block 66 along its guide path S (of FIG. 1) so that the organic alloy specimen contained therein passes from the melting zone over the copper heating source 22 (FIG. 1) and into the freezing zone over the copper cooling sink 20 (of FIG. 1). The temperature of the copper heating source 22 and the copper cooling sink 20, as well as the temperature of the liquid coolant are all controlled such that while the temperature gradient can be varied, as well as the pusher rod 106 velocity, the freezing isotherm will always remain under the view of the fixed position microscope 30 in the gap 42.

Referring now to FIG. 7 there is shown a block diagram of the electronics of the system. In FIG. 7 the only input is the output signals from the thermocouples 84 and 86 of FIG. 6 via leads 88 and 90 to multiplexor 120 of FIG. 7. The multiplexed output of multiplexor 120 is amplified by amplifier 122 and then supplied to analog-to-digital (A/D) converter 124 whose digitized output is supplied to a suitable computer such as an Apple II which is programmed to provide to digital-to-analog (D/A) converter analog signals which, when multiplexed by multiplexor 130, will supply the proper control signals for ultimately controlling the temperatures of copper heating source block 22 of FIGS. 1 and 2 and copper cooling sink 20 of FIGS. 1 and 2, as well as the speed of motor 104 of FIG. 6.

More specifically, the S/H circuits 98, 100, and 102, also shown in FIG. 6 which will now again be referred to, control the d.c. power generated by d.c. power sources 92, 94, and 96, respectively, which supply d.c. currents to thermoelectric heaters 44 and 46 of FIG. 2 and motor 104 of FIG. 6. The function of motor 104, gear box 108, and pusher rod 106 have already been discussed.

A monitor 134 such as a visual display, a printer 136, and a double density (DD) floppy disc unit 138 are connected to the computer 126 to observe the parameters of heating sources, cooling sources, temperature gradient across gap 42, position of the freezing isotherm, and pusher rod velocity.

It is to be noted that the computer 126 is programmed not only to control the temperature gradient across gap 42 but also to control the rate and amount of change of such temperature gradient, and further to maintain the freezing isotherm in gap 42 in FIG. 2 under the view of microscope 30.

A generalized summary of the invention, its operation and some other features not specifically set forth above are set forth in the following paragraphs. With the device of this invention, one end of a specimen cell is heated to exceed the melting point of the material contained within, while the other end is cooled to a frozen condition. Thermal contact of the cell against a hot metal block 22 (FIG. 2) and a cold metal block 20 (FIG. 2) separated by a narrow gap 42 provides the desired temperature gradient G within the cell. The respective temperatures of the blocks are controlled to cause the solid-liquid interface to develop midway between the heating and cooling blocks in gap 42.

Structural details of this interface between solid and liquid are generally studied with an optical microscope. The specimen is transilluminated through the gap 42 between the hot and cold blocks. Interface details are rendered in contrast by optical diffraction effects at the interfaces. The specimen itself is a sandwich with the transparent specimen material held as a thin film between two glass slides. The material, which is the specimen of interest, must have a melting temperature compatible with the capability of the apparatus. (Presently this range is approximately −20 to +100 C.) Materials are selected based on their solidification characteristics. The best choices are models which have metal-like solidification characteristics.

Studying G/R ratio effects by varying R alone does not lend itself to simple interpretation. Crystal growers know that as one varies the velocity rate R, the kinetic undercooling seen by the growing interface will vary. A comprehensive study of interface kinetics has never been done heretofar because of the above limitations. However, varying the temperature gradient G at a constant R essentially controls the driving force (i.e. thermodynamics) for solidification while keeping a constant kinetic dependence.

The stage is made up of a hot metal block 22 (FIG. 2) and a cold metal block 20, (FIG. 2) whose individual temperatures are each controlled by a thermoelectric pile. The temperatures are monitored by thermocouples 84 and 86 (FIG. 6) in the metal blocks and the signals used to regulate the power going into each of the thermoelectric devices. In the present model, the sensing and control functions are controlled by a microcomputer 126. Other temperature controller devices can be used as well. The thermoelectric devices are each cooled by a constant temperature water bath. The temperature of the bath is set to the melting temperature of the specimen being observed. By this method, one thermoelectric device is used for cooling relative to the melting temperature and the other is used for heating. To adjust the temperature gradient, the d.c. current to each thermoelectric is increased or decreased so that the block temperatures track at preprogrammed rates. As this occurs, the specimen cell is pushed at a constant rate across the heating and cooling blocks in the direction of the cold block to thereby cause the specimen to freeze undirectionally. In the working model, the push rate is also computer controlled. Observations of the interface are made at this time and may be recorded.

It is essential to have thermal stability in the apparatus. Earlier temperature gradient stages did not have variable temperature gradients and achieved thermal stability by using much larger thermal masses for the hot and cold metal blocks 22 and 20 (FIG. 2). This prior art method to stabilize the temperature cannot be used here as the rate of changing the gradient G must be smooth and rapid (e.g. two deg. C per cm. per minute). Therefore, to compensate for the low thermal mass of the blocks, tighter temperature control is needed. This is achieved in the present invention by using the constant temperature circulating water bath and trimming the temperatures with the thermoelectric heaters (devices) which are controlled by the computer and regulated power supplies. In the present invention the computer calculates the needed current to run the thermoelectric heaters, then this calculation is sent out via the D/A converter 128 (FIG. 7) to the S/H amplifiers 98, 100, and 102 which provide a control signal to the high current d.c. power supplies.

It is to be understood that the form of the invention shown and described herein is but one preferred form thereof and that various other modifications and forms thereof will be apparent to one of ordinary skill in the art without the exercise of invention and are intended to lie within the scope of the claims appended hereto.

I claim:

1. A method of investigating the formation of crystals in a transparent specimen material comprising the steps of:
    melting the transparent specimen material in a fixed position heating zone;
    forming a freezing isotherm to freeze the transparent specimen material in a gap positioned between a fixed position cooling zone which is separated from said heating zone by said gap by a predetermined distance capable of containing said freezing isotherm with suitable temperatures of said heating and cooling zones;
    moving the transparent specimen material from said heating zone to said cooling zone;
    varying the temperature of said heating zone and said cooling zone to create a variable temperature gradient across said gap and to maintain the freezing isotherm of said transparent specimen material in said gap in a substantially fixed position relative to said heating and cooling zones; and
    observing the freezing isotherm of the transparent specimen material through an optically enlarging means to watch and analyze the formation of dendrites in said freezing isotherm of said transparent specimen material as the temperature of said heating and cooling zones are varied to produce said variable temperature gradient across said gap and therefore across said freezing isotherm.

2. A method as in claim 1 and comprising the further steps of:
    placing the specimen between two sheets of glass before performing said melting step of claim 1;
    placing the glass contained specimen in position for being heated and then cooled as set forth in claim 1;
    selectively pushing the glass contained specimen to move said specimen through said gap from the heating zone and into the cooling zone to enable observation of the freezing of the specimen in the freezing isotherm which remains in the gap as the transparent specimen moves through said gap.

3. A method as in claim 1 in which said melting step comprises the further steps of:
    circulating a bath of liquid coolant through said heating zone to aid in controlling the temperature of said heating zone in a manner to make the temperature of said heating zone constant throughout said heating zone
    heating said heating zone which can be of copper or other good heat conducting material to a desired temperature by thermoelectric devices;
    measuring the temperature of said heating zone by temperature measuring means such as thermocouples; and
    controlling the temperature of said heating zone by controlling the current through said thermoelectric devices in response to the temperature of said heating zone as measured by said temperature measuring means.

4. A method as in claim 1 in which said freezing step comprises the further steps of:
    circulating a bath of liquid coolant through said cooling zone to aid in controlling the temperature of said cooling zone in a manner to make the temperature of said cooling zone constant throughout said cooling zone
    heating said cooling zone, which can be of copper or other good heat conducting material, to a desired temperature by thermoelectric devices;

measuring the temperature of said cooling zone by temperature measuring means such as thermocouples; and controlling the temperature of said cooling zone by controlling the current through said thermoelectric devices in response to the temperature of said cooling zone as measured by said temperature measuring means.

5. A method of observing crystal formation in a transparent specimen comprising the steps of:

melting a portion of the specimen in a heating zone;

forming a freezing isotherm to freeze the melted portion of the specimen by the action of a cooling zone spaced from said heating zone by a gap which is observable by a suitable observing means;

controlling the temperatures of said heating and cooling zones to various temperatures and the length of said gap to create a variable temperature gradient across said gap so that the freezing isotherm of said specimen always remains in a constant position in said gap where it is observable by said observing means; and moving said specimen longitudinally across said gap while said temperature gradient is varying to enable observation of the constantly newly formed freezing portion of the specimen occurring in the gap as the specimen is moved therethrough.

6. A method as in claim 5 and comprising the further steps of:

placing the specimen between two sheets of glass before performing said melting step of claim 5;

placing the glass contained specimen in position for being heated and then cooled as set forth in claim 5;

selectively pushing the glass contained specimen to move said specimen through said gap from said heating zone and into said cooling zone to enable observation of the freezing of the specimen in the freezing isotherm which remains in the gap as the specimen moves through said gap.

7. A method as in claim 5 in which said melting step comprises the further steps of:

circulating a bath of liquid coolant through said heating zone to aid in making the temperature of said heating zone constant through out said heating zone;

heating said heating zone, which can be of copper or other good heat conducting materials, to a desired temperature by thermoelectric devices;

measuring the temperature of said heating zone by temperature measuring means such as thermocouples;

controlling the temperature of said heating zone by controlling the current through said thermoelectric devices in response to the temperature of said heating zone as measured by said temperature measuring means.

8. A method as in claim 5 in which said feezing step comprises the further steps of:

circulating a bath of liquid coolant through said cooling zone to aid in controlling the temperature of said cooling zone in a manner to make the temperature of said cooling zone constant throughout said cooling zone;

heating said cooling zone, which can be of copper or other good heat conducting material, to a desired temperature by thermoelectric devices;

measuring the temperature of said cooling zone by temperature measuring means such as thermocouples; and controlling the temperature of said cooling zone by controlling the current through said thermoelectric devices in response to the temperature of said cooling zone as measured by said temperature measuring means.

9. A method for observing crystal formation in a specimen comprising the steps of:

moving the specimen at a controlled and variable speed from a controlled temperature heating zone to melt the rod and through a small, predetermined gap to a controlled temperature cooling zone to create a temperature gradient of sufficient slope and range to create a freezing isotherm in said gap at all times to freeze the specimen into a predetermined unitary solid shape; and varying the temperatures of said heating and cooling zones in a controlled manner to maintain the freezing isotherm of said specimen within said gap for observation while the specimen is moving through said gap.

10. A method as in claim 9 in which said temperature varying step comprises the further steps of:

circulating a bath of liquid coolant through said heating zone to aid in controlling the temperature of said heating zone in a manner to make the temperature of said heating zone constant throughout said heating zone;

heating said heating zone, which can be of copper or other good heat conducting material, to a desired temperature by thermoelectric devices;

measuring the temperatures of said heating zone by temperatures measuring means such as thermocouples; and controlling the temperature of said heating zone by controlling the current through said thermoelectric devices in response to the temperature of said heating zone as measuring by said temperature measuring means.

11. A method as in claim 9 and comprising the further steps of:

placing the specimen between two sheets of glass before performing the said moving step of claim 9;

placing the glass contained specimen in position for being heated and then cooled as set forth in claim 9; and selectively pushing the glass containing specimen to move said specimen through said gap from the heating zone and into the cooling zone to enable observation of the freezing of the specimen in the freezing isotherm which remains in the gap as the glass containing specimen moves through said gap.

12. A method as in claim 9 in which said heating step comprises the further steps of:

circulating a bath of liquid coolant through said cooling zone to aid in controlling the temperature of said heating zone constant throughout said cooling zone;

heating said cooling zone, which can be of copper or other good heat conducting material, to a desired temperature by thermoelectric devices;

measuring the temperature of said cooling zone by temperature measuring means such as thermocouples; and controlling the temperature of said cooling zone by controlling the current through said thermoelectric devices in response to the temperature of said cooling zone as measured by said temperature measuring means.

13. Apparatus for investigating the formation of crystals in a transparent specimen material comprising:
a fixed position heating zone and a fixed position cooling zone;
first means for melting the transparent specimen material in said fixed position heating zone;
second means for freezing the transparent specimen material in said fixed position cooling zone which is separated from said heating zone by a gap of a predetermined small distance to maintain a freezing isotherm for said specimen material therein;
third means for moving the specimen material from said heating zone to said cooling zone;
fourth means for controllably varying the temperature of said heating zone and said cooling zone in a manner to create a variable temperature gradient across said gap and to maintain the freezing isotherm of said transparent specimen material in said gap in a substantially fixed position relative to said heating and cooling zones; and
suitable observing means for observing the freezing isotherm of said transparent specimen material to watch and analyze the formation of crystals in said freezing isotherm of said transparent specimen material as the temperature of said heating and cooling zones are varied to produce a variable temperature gradient across said gap and therefore across said freezing isotherm.

14. Apparatus as in claim 13 and further comprising:
two sheets of glass sealed together around their edges and with said specimen positioned therebetween; and
means for selectively pushing the glass contained specimen to move said specimen through the freezing isotherm positioned in said gaps from said heating zone and into the cooling zone.

15. Apparatus as in claim 13 in which said first means further comprises:
fifth means for circulating a bath of liquid coolant through said heating zone to aid in controlling the temperature of said heating zone in a manner to make the temperature of said heating zone constant throughout said heating zone;
sixth means such as thermoelectric devices for heating said heating zone, which can be comprised of copper or other good heat conducting material, to a desired temperature by said thermoelectric devices;
seventh means such as thermocouples for sensing and measuring the temperature of said heating zone; and
eighth means for controlling the temperature of said heating zone by controlling the current through said thermoelectric devices in response to the temperature of said heating zone as sensed and measured by said seventh means.

16. Apparatus as in claim 13 in which said second means further comprises:
fifth means for circulating a bath of liquid coolant through said heating zone to aid in controlling the temperature of said cooling zone in a manner to make the temperature of said cooling zone constant throughout said cooling zone;
sixth means such as thermoelectric devices for heating said cooling zone, which can be comprised of copper or other good heat conducting material, to a desired temperature by said thermoelectric devices;
seventh means such as thermocouples for sensing and measuring the temperature of said heating zone; and
eighth means for controlling the temperature of said heating zone by controlling the current through said thermoelectric devices in response to the temperature of said heating zone as sensed and measured by said seventh means.

17. Apparatus for observing crystal formation in a specimen comprising:
a heating zone and cooling zone separated by a gap in which a temperature gradient containing a freezing isotherm for said specimen can be created continuously by controlling the temperatures of said heating and cooling zones;
first means for moving the specimen at a controlled and variable speed from said heating zone to melt said specimen and through said gap to said cooling zone to freeze said specimen; and
second means for varying the temperature of said heating and cooling zones in a controlled manner to create a controlled variable temperature gradient in said gap and to maintain the freezing isotherm of said specimen in said gap.

18. Apparatus as in claim 17 and further comprising:
two sheets of glass sealed together around their edges and with said specimen positioned therebetween; and
means for selectively pushing the glass contained specimen to move said specimen through the gap containing said freezing isotherm from said heating zone and into the cooling zone.

19. Apparatus as in claim 17 in which said second means further comprises:
third means for circulating a bath of liquid coolant through said heating zone to aid in controlling the temperature of said heating zone in a manner to make the temperature of said heating zone constant throughout said heating zone;
fourth means such as thermoelectric devices for heating said heating zone, which can be comprised of copper or other good heat conducting material, to a desired temperature by thermoelectric devices;
fifth means such as thermocouples for sensing and measuring the temperature of said heating zone; and
sixth means controlling the temperature of said heating zone by controlling the current through said thermoelectric devices in response to the temperature of said heating zone as sensed and measured by said fifth means.

20. Apparatus as in claim 17 in which said second means further comprises:
third means for controlling the temperature of said cooling zone in a manner to make the temperature of said cooling zone constant throughout said cooling zone;
fourth means such as thermoelectric devices for heating said cooling zone, which can be comprised of copper or other good heat conducting material, to a desired temperature by said thermoelectric devices;
fifth means such as thermocouples for sensing and measuring the temperature of said cooling zone; and
sixth means controlling the temperature of said cooling zone by controlling the current through said thermoelectric devices in response to the temperature of said cooling zone as sensed and measured by said fifth means.

* * * * *